United States Patent [19]

Rizkalla

[11] 4,335,058

[45] Jun. 15, 1982

[54] PREPARATION OF CARBOXYLIC ACID ANHYDRIDES

[75] Inventor: Nabil Rizkalla, River Vale, N.J.

[73] Assignee: Halcon Research and Development Corp., New York, N.Y.

[21] Appl. No.: 267,962

[22] Filed: May 28, 1981

Related U.S. Application Data

[63] Continuation-in-part of Ser. No. 219,788, Dec. 24, 1980.

[51] Int. Cl.³ .................... C07C 51/56; C07C 51/54; C07C 53/12
[52] U.S. Cl. .................................................... 260/546
[58] Field of Search ...................................... 260/5 46

[56] References Cited

U.S. PATENT DOCUMENTS

| 2,549,453 | 4/1951 | Gresham et al. | 260/546 |
| 2,593,440 | 4/1952 | Hagemeyer, Jr. | 260/546 |
| 2,768,968 | 10/1956 | Reppe et al. | 260/546 |

Primary Examiner—Natalie Trousof
Assistant Examiner—Frederick W. Pepper
Attorney, Agent, or Firm—William C. Long; Riggs T. Stewart; Harold N. Wells

[57] ABSTRACT

A carboxylic acid anhydride, such as propionic anhydride, is prepared from an olefin and a carboxylic acid in carbonylation processes comprising the use of a halide, carbon monoxide and a molybdenum-nickel or tungsten-nickel component in the presence of a promoter comprising an organo-phosphorus compound or an organo-nitrogen compound wherein the phosphorus and nitrogen are trivalent.

4 Claims, No Drawings

PREPARATION OF CARBOXYLIC ACID ANHYDRIDES

REFERENCE TO RELATED APPLICATION

This is a continuation-in-part of co-pending application Ser. No. 219,788 filed Dec. 24, 1980.

This invention relates to the preparation of anhydrides of carboxylic acids, more particularly mono-carboxylic acids and especially the anhydrides of lower alkanoic acids, such as propionic anhydride, by the carbonylation of olefins.

The production of anhydrides by the action of carbon monoxide upon olefins (carbonylation) has been described, for example, in Reppe et al. U.S. Pat. No. 2,768,968. However, this proposal requires the use of very high pressures. In later patents, carbonylation of olefin at lower pressures has been proposed. Foster et al. U.S. Pat. No. 3,852,346 describes the carbonylation of olefins in the presence of compounds of Group VIII noble metals such as iridium and rhodium and in the presence of an iodide under more moderate pressures than those contemplated by Reppe et al.

However, this process suffers from the need to employ expensive, relatively rare metals.

It is an object of the present invention to provide an improved process for the manufacture of carboxylic acid anhydrides from olefins, especially lower alkanoic anhydrides, such as propionic anhydride, which requires neither high pressures nor Group VIII noble metals.

In accordance with the invention, carbonylation of an olefin is carried out by using a molybdenum-nickel or a tungsten-nickel co-catalyst in the presence of a promoter comprising an organo-phosphorus compound or an organo-nitrogen compound where-in the phosphorus and nitrogen are trivalent, and in the presence of a halide, preferably an iodide, a bromide, and/or a chloride, especially an iodide, and in the presence of a carboxylic acid. The surprising discovery has been made that this co-catalyst in combination with the promoter-halide system of the character indicated makes possible carbonylation of olefins not only at relatively low pressures but with rapid, high yield production of carboxylic acid anhydrides.

Thus, in accordance with the invention, carbon monoxide is reacted with an olefin, especially a lower alkene, to produce a carboxylic anhydride, such as a lower alkanoic anhydride, the carbonylation taking place in the presence of a halide, e.g., a hydrocarbyl halide, especially a lower alkyl halide, such as ethyl iodide, and a carboxylic acid. Thus, propionic anhydride, for example, can be effectively prepared in a representative case by subjecting ethylene to carbonylation in the presence of ethyl iodide and in the presence of propionic acid. In all cases, the carbonylation is carried out under anhydrous conditions in the presence of the co-catalyst promoter-system described above.

It will be understood that the halide moiety does not have to be added to the system as a hydrocarbyl halide but may be supplied as another organic halide or as the hydrohalide or other inorganic halide, e.g., a salt, such as the alkali metal or other metal salt, or even as the elemental halide, e.g. elemental iodine. Following the reaction, the organic components of the reaction mixture are readily separated from one another, as by fractional distillation.

In like manner, other lower alkanoic anhydrides, i.e., anhydrides of lower alkanoic acids, such as i-butyric anhydride, n-butyric anhydride, and valeric anhydride, can be produced by carbonylating the corresponding lower alkene. Similarly, other carboxylic acid anhydrides, e.g., the anhydrides of other alkanoic acids, for example, capric anhydrides, caprylic anhydrides and lauric anhydrides, and like higher anhydrides are produced by carbonylating the corresponding olefin.

The reactant olefin may be any ethylenically unsaturated hydrocarbon having from 2 to about 25 carbon atoms, preferably from 2 to about 15 carbon atoms. The ethylenically unsaturated compound has the following general structure:

$$R_2R_1C = CR_3R_4$$

wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1,2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene, 1-allyl-3-vinylbenzene, etc. Of the olefins referred to above, the alpha hydrocarbon olefins and olefins having 2 to about 10 carbon atoms are preferred, e.g., ethylene, propylene, butene-1, hexene-1, heptene-1, octene-1, and the like, i.e. wherein $R_1$, $R_2$, $R_3$ and $R_4$ are hydrogen or alkyl groups totalling 1–8 carbon atoms, preferably the lower alkenes, i.e. alkenes of 2 to 6 carbon atoms, especially ethylene.

The reactant carboxylic acid may be in general any carboxylic acid having 1 to about 25 carbons and having the formula:

$$RCOOH$$

wherein R is hydrogen, alkyl, cycloalkyl or aryl. Preferably R has 1 to about 18 carbon atoms and most preferably R is alkyl having 1 to about 12 carbon atoms, especially 1 to 6 carbon atoms e.g., methyl, ethyl, propyl, isobutyl, hexyl, nonyl, and the like, or is aryl with 6 to about 9 carbon atoms, e.g., phenyl, tolyl, and the like.

Examples of useful acids are acetic, propionic, n-butyric, isobutyric, pivalic, n-valeric, n-caproic, caprylic, capric, decanoic, myristic, palmitic, naphthoic, stearic, benzoic, phthalic, terephthalic, toluic, 3-phenylhexanoic acid, 2-xylylpalmitic acid and 4-phenyl-5-isobutyl stearic acid. The preferred acids are the fatty or alkanoic acids having 2 to about 12 carbon atoms, e.g., acetic, propionic, n-butyric, isobutyric, pivalic, caproic, undecylic, and the like. Especially preferred are the lower alkanoic acids i.e. wherein R is an alkyl group of 1 to 6 carbon atoms, expecially propionic acid. R can be branched and can be substituted with substituents which are inert in the reactions of the invention.

It is preferred that the reactants be selected so that the resulting anhydride will be a symmetrical anhydride, i.e., having two identical acyl groups.

In the most preferred embodiment of the invention carbon monoxide is reacted with ethylene and propionic acid in the presence of the co-catalyst-promoter-halide system of the character described above to produce propionic anhydride in a reaction which may be expressed as follows:

$$C_2H_4 + CO + C_2H_5COOH \rightarrow C_2H_5COOCOC_2H_5$$

Carbon monoxide is removed in the vapor phase along with unreacted olefin when the olefin is normally gaseous, e.g., ethylene and, if desired, recycled. Normally liquid and relatively volatile components such as alkyl halide and unreacted normally-liquid olefin and carboxylic acid and by-products present in the final product mixture can be readily removed and separated from each other, as by distillation, for recycling, and the net yield of product is substantially exclusively the desired carboxylic anhydride. In the case of liquid-phase reaction, which is preferred, the organic compounds are easily separated from the metal-containing components, as by distillation. The reaction is suitably carried out in a reaction zone to which the carbon monoxide, the olefin, the acid, the halide, the specified co-catalyst and the promoter are fed. No water is produced in the above-described reactions and anhydrous conditions are employed.

In carrying out the process of the invention, a wide range of temperatures, e.g., 25° to 350° C. are suitable but temperatures of 80° to 250° C. are preferably employed and the more preferred temperatures generally lie in the range of 110° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 2,000 psi and most preferably 30 to 1,200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time, the reaction mixture is separated into several constituents, as by distillation. Preferably, the reaction product is introduced into a distillation zone which may be a fractional distillation column, or a series of columns, effective to separate the volatile components from the product anhydride catalyst and promoter components of the reaction mixture. The boiling points of the volatile components are sufficiently far apart that their separation by conventional distillation presents no particular problem. Likewise, the higher boiling organic components can be readily distilled away from the metal co-catalyst components and any organic promoter which may be in the form of a relatively non-volatile complex. The co-catalyst components, and promoter can then be combined with fresh amounts of olefin, carboxylic acid and carbon monoxide and reacted to produce additional quantities of anhydride.

Although not necessary, the process can be carried out in the presence of a solvent or diluent. The presence of a higher boiling solvent or diluent, which may be the product anhydride itself, e.g., propionic anhydride in the case of ethylene will make it possible to employ more moderate total pressure. Alternatively, the solvent or diluent may be any organic solvent which is inert in the environment of the process such as hydrocarbons, e.g., octane, benzene, toluene, or carboxylic acids, e.g., propionic acid, and the like. Excess carboxylic acid, when used as a solvent should correspond to the carboxylic acid being reacted. A solvent or diluent is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those above mentioned.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or molybdenum, tungsten or nickel carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl.

Included among the catalyst components listed above are complexes of the metal co-catalyst components with organic promoter ligands derived from the organic promoters hereinafter described. Particularly preferred are the elemental forms, compounds which are iodides, and organic salts, e.g., salts of the monocarboxylic acid corresponding to the anhydride being produced. It will be understood that the foregoing compounds and complexes are merely illustrative of suitable forms of the several co-catalyst components and are not intended to be limiting.

The specified co-catalyst components employed may contain impurities normally associated with the commercially available metal or metal compounds and need not be purified any further.

The organo-phosphorus promoter is preferably a phosphine, e.g., a phosphine of the formula

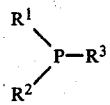

wherein $R^1$, $R^2$ and $R^3$ may be same or different, and are alkyl, cycloalkyl, aryl groups, amide groups or halogen atoms, preferably containing up to 1 to 20 carbon atoms in the case of alkyl and cycloalkyl groups and 6 to 18 carbon atoms in the case of aryl groups. Typical phosphines include trimethylphosphine, tripropylphosphine, tricyclohexylphosphine and triphenylphosphine.

Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexyl-methylamine, 2,6-diaminopyridine, 2-quinolinol, N,N-diethyltoluamide, imidazole, pyridine, picolines and the like.

Although generally the organic promoters are added separately to the catalyst system, it is also possible to add them as complexes with the co-catalyst metals such as bis(triphenylphosphine) nickel dicarbonyl, and tetrakis (triphenyl phosphite) nickel. Both free organic promoters and complexed promoters can also be used. Indeed, when a complex of the organic promoter and the nickel and/or co-catalyst components are used, free organic promoter can also be added as well.

The amount of each co-catalyst component is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each component of the co-catalyst is employed in the amount of 1 millimol to 1 mol per liter of reaction mixture, preferably 5 millimols to 500 millimols per liter and most preferably 15 millimols to 150 millimols per liter.

The ratio of nickel to its co-catalyst component can vary. Typically, it is one mol of nickel per 0.01 to 100 mols of the other co-catalyst component, preferably the nickel component is used in the amount of 1 mol per 0.1 to 20 mols, most preferably 1 mol per 1 to 10 mols of the other co-catalyst component.

The quantity of organic promoter can also vary widely but typically it is used in the amount of 1 mol per 0.1 to 10 mols of co-catalyst components, preferably 1 mol per 0.5 to 5 mol, most preferably 1 mol per 1 to 5 mols of co-catalyst components.

As previously mentioned, in the working up of the reaction mixtures, e.g., by distillation, the promoter components can be readily recovered and recycled to the reaction. The nickel and co-catalyst metal generally remain as the least volatile components, and are recycled or otherwise handled together. They may, however, distill with the volatile components, e.g., in the case of nickel carbonyl. The same is true of the promoter components.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 200 mols of halide per mol of nickel are not used.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid anhydride, with the other organic components being recycled and, in the case of liquid-phase reaction, a residual nickel co-catalyst-containing (and promoter-containing) fraction also being recycled.

A particular embodiment of the catalyst comprising the molybdenum-nickel or tungsten-nickel co-catalyst component, the organic promoter component and the halide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is an organophosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

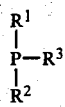

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1, preferably 5–100:1. The halide is chloride, bromide or iodide, preferably iodide.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported. i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts and all percentages are by weight, unless otherwise indicated.

EXAMPLE 1

A magnetically-stirred pressure vessel with a glass liner is charged with 250 parts propionic acid, 50 parts iodoethane, 3 parts nickel iodide, 6 parts molybdenum hexacarbonyl, and 15 parts triphenyl phosphine. The vessel is swept out with argon and is pressured to 100 p.s.i.g. with hydrogen and up to 400 p.s.i.g. with carbon monoxide. The vessel is heated to 172° C. with stirring. The pressure is brought up to 750 p.s.i.g. using a 1:1 mixture of ethylene and carbon monoxide. The pressure is maintained at 750 p.s.i.g. by recharging a 1:1 mixture of ethylene and carbon monoxide. The temperature is maintained at 172° C. After one hour of reaction, G.C. analysis of the reaction mixture shows it to contain 42 wt.% propionic anhydride. The reaction mixture weighs more than the charge by 89 parts, showing an increase in weight by that amount.

EXAMPLE 2

Example 1 is repeated with the exception that molybdenum hexacarbonyl is replaced with an equivalent quantity of tungsten hexacarbonyl. After one hour of reaction, G.C. analysis of the reaction mixture shows it to contain 37 wt.% propionic anhydride. The reaction mixture shows a weight increase of 78 parts.

EXAMPLE 3

Example 1 is repeated with the exception that molybdenum hexacarbonyl is replaced with an equivalent quantity of molybdenum acetate. After 1 hour of reaction, G.C. analysis of the reaction mixture shows it to contain 39 wt.% propionic anhydride. The reaction mixture shows a weight increase of 82 parts.

EXAMPLE 4

Example 1 is repeated with the exception that nickel iodide is replaced with nickel acetate. After one hour of reaction, G.C. analysis shows it to contain 39 wt.% propionic anhydride. The reaction mixture shows a weight increase of 82 parts.

EXAMPLE 5

Example 1 is repeated with the exception that it is run at 155° C. After 4 hours of reaction, G.C. analysis shows the reaction mixture to contain 60.6 wt.% propionic anhydride. The reaction mixture shows a weight increase of 146 parts.

EXAMPLE 6

A magnetically-stirred pressure vessel with a glass liner is charged with 250 parts propionic acid, 10 parts concentrated hydrochloric acid, 6 parts bis triphenyl phosphine nickel dicarbonyl, 6 parts molybdenum hexacarbonyl and 15 parts triphenyl phosphine. The vessel is swept out with argon and is pressured to 106 p.s.i.g. with hydrogen and up to 400 p.s.i.g. with carbon monoxide. The vessel is heated to 180° C. with stirring. The pressure is brought up to 800 p.s.i.g. using 1:1 mixture of ethylene and carbon monoxide. The pressure is maintained at 800 p.s.i.g. by recharging a 1:1 mixture of ethylene and carbon monoxide. The temperature is maintained at 180° C. After 2 hours and fifteen minutes, G.C. analysis of the reaction mixture shows it to contain 11 wt.% propionic anhydride. The reaction mixture shows a weight increase of 43.7 parts.

EXAMPLE 7

Example 6 is repeated with the exception that the hydrochloric acid is replaced with an equal weight of hydrobromic acid. The reaction is run for 2 hours at 160° C. and under a total pressure of 800 p.s.i.g., then the temperature is increased to 180° C. while the pressure is maintained at 800 p.s.i.g. using a 1:1 mixture of ethylene and carbon monoxide. After one hour and 45 minutes of reaction at 180° C., G.C. analysis shows the reaction mixture to contain 39.2 wt.% propionic anhydride. The reaction mixture shows a weight increase of 79.5 parts.

EXAMPLE 8

A magnetically-stirred pressure vessel with a glass liner is charged with 250 parts propionic acid, 20 parts ethyl iodide 3 parts nickel iodide, 6 parts molybdenum carbonyl, and 15 parts triphenylphosphine. The vessel is swept out with argon and is pressured to 100 p.s.i.g. with hydrogen and up to 400 p.s.i.g. with hydrogen and up to 400 p.s.i.g. with carbon monoxide. The vessel is then heated to 157° C. with stirring. The pressure is brought up to 750 p.s.i.g. using a 1:1 mixture of ethylene and carbon monoxide. The pressure is maintained at 75 p.s.i.g. by recharging a 1:1 mixture of ethylene and carbon monoxide, and the temperature is maintained at 157° C. After one hour of reaction, G.C. analysis of the reaction mixture shows it to contain 37.5 wt.% propionic anhydride. The reaction mixture shows a weight increase of 51 parts.

EXAMPLE 9

Example 8 is repeated with the exception that the temperature used is 131° C. After 2 hours of reaction, G.C. analysis shows the reaction mixture to contain 36 wt.% propionic anhydride. The reaction mixture shows a weight increase of 64.5 parts.

EXAMPLE 10

A magnetically-stirred pressure vessel with a glass liner is charged with 250 parts propionic acid, 50 parts iodoethane, 3 parts nickel iodide, 6 parts molybdenum hexacarbonyl and 20 parts triphenyl phosphine. The vessel is swept out with argon and is pressured to 25 p.s.i.g. with hydrogen and up to 125 p.s.i.g. with carbon monoxide. The vessel is heated to 175° C. with stirring. The pressure is brought up to 350 p.s.i.g. under a 1:1 mixture of ethylene and carbon monoxide. The pressure is maintained at 350 p.s.i.g. by recharging a 1:1 mixture of ethylene and carbon monoxide, and the temperature is maintained at 175° C. After 3 hours of reaction, G.C. analysis of the reaction mixture shows it to contain 20 wt.% propionic anhydride. The reaction mixture shows a weight increase of 30.3 parts.

EXAMPLE 11

A magnetically-stirred pressure vessel with a glass liner charged with 250 parts propionic acid, 20 parts chloroethane, 6 parts bis-triphenylphosphine nickel dicarbonyl, 9 parts molybdenum hexacarbonyl, and 20 parts triphenylphosphine. The vessel is swept out with argon and is pressured to 100 p.s.i.g. with hydrogen and up to 300 p.s.i.g. with carbon monoxide. The vessel is then heated to 175° C. with stirring. The pressure is brought up to 750 p.s.i.g. using a 1:1 mixture of ethylene and carbon monoxide and the pressure is maintained at 750 p.s.i.g. by recharging a 1:1 mixture of ethylene and carbon monoxide as needed and the temperature is maintained at 175° C. After 2 hours and 45 minutes of reaction, G.C. analysis of the reaction mixture shows it to contain 23 wt. % propionic anhydride. The reaction mixture shows a weight increase of 33 parts.

EXAMPLE 12

Example 11 was repeated with the exception rhat the chloroethane is replaced with an equal amount of bromoethane. The reaction is run at 175° C. and 630 p.s.i.g. total pressure. After 3 hours of reaction, G. C. analysis of the reaction mixture shows it to contain 53 wt. % propionic anhydride. The reaction mixture shows a weight increase of 72 parts.

EXAMPLE 13

A magnetically-stirred pressure vessel with a glass liner was charged with 250 parts propionic acid, 50 parts iodoethane, 6 parts nickel iodide, 10 parts molybdenum hexacarbonyl, and 5 parts pyridine. The vessel is swept out with argon and is pressured to 100 p.s.i.g. with hydrogen and up to 400 p.s.i.g. with carbon monoxide. The vessel is then heated to 175° C. with stirring. The pressure is brought up to 700 p.s.i.g. using a 1:1 mixture of ethylene and carbon monoxide and the pressure is maintained at 700 p.s.i.g. by recharging a 1:1 mixture of ethylene and carbon monoxide. The temperature is maintained at 175° C. After 2 hours and 20 minutes of reaction, G.C. analysis of the reaction mixture shows it to contain 62 wt.% propionic anhydride. The reaction mixture shows a weight increase of 108 parts.

EXAMPLE 14

Example 13 is repeated with the exception that the pyridine is replaced with an equal amount of 2-picoline. After 1 hour of reaction, G.C. analysis shows the reaction mixture to contain 39 wt.% propionic anhydride. The reaction mixture shows a weight increase of 82 parts.

EXAMPLE 15

A pressure vessel as described in Example 1 is charged with 250 parts propionic acid, 6 parts nickel dichloride ($NiCl_2.6H_2O$), 10 parts molybdenum hexacarbonyl and 20 parts triphenyl phosphine. The vessel is swept out with argon and is pressured to 100 p.s.i.g. with hydrogen and up to 400 p.s.i.g. with carbon monoxide, and the vessel is heated to 175° C. with stirring. The pressure is brought up to 550 p.s.i.g. using a 1:1 mixture of ethylene and carbon monoxide and the pressure was maintained at 550 p.s.i.g. by recharging a 1:1 mixture of ethylene and carbon monoxide. The temperature was maintained at 175° C. After 3 hours of reaction, G.C. analysis of the reaction mixture shows it to contain 53 wt.% propionic anhydride. The reaction mixture shows a weight increase of 89 parts.

EXAMPLE 16

A pressure vessel as described in Example 1 is charged with 250 parts propionic acid, 20 parts iodoethane, 3 parts nickel iodide, 6 parts molybdenum carbonyl and 5 parts pyridine. The vessel is swept out with argon and is pressured to 400 p.s.i.g. with carbon monoxide and is then heated to 175° C. with stirring. The pressure is brought up to 830 p.s.i.g. by means of ethylene and the pressure is maintained at 800 p.s.i.g. by recharging a 1:1 mixture of ethylene and carbon monoxide. The temperature is maintained at 175° C. After 3 hours of reaction, G. C. analysis of the reaction mixture shows it to contain 52% propionic anhydride.

COMPARATIVE EXAMPLE A

Example 10 is repeated except that molybdenum hexacarbonyl is omitted from the charge. No gas absorption is observed. G.C. analysis of the reaction effluent indicates that it contains 1% propionic anhydride.

What is claimed is:

1. A process for the preparation of carboxylic acid anhydrides which comprises reacting an olefin and a carboxylic acid with carbon monoxide in the presence of a catalytically-effective quantity of a molybdenum-nickel or tungsten-nickel co-catalyst component, in the presence of a halide and in the presence of a promoter comprising an organo-phosphorus compound or an organo-nitrogen compound wherein the phosphorus and nitrogen are trivalent.

2. A process as defined in claim 1, wherein the co-catalyst component comprises molybdenum-nickel.

3. A process as defined in claim 1, wherein the promoter is a phosphine.

4. A process as defined in claim 1, wherein the co-catalyst comprises molybdenum-nickel and the promoter is a phosphine.

* * * * *

UNITED STATES PATENT AND TRADEMARK OFFICE
CERTIFICATE OF CORRECTION

PATENT NO. : 4,335,058
DATED : June 15, 1982
INVENTOR(S) : Nabil Rizkalla

It is certified that error appears in the above-identified patent and that said Letters Patent is hereby corrected as shown below:

Col. 8, line 54 - "75" should be --750--

Col. 9, line 10 - "under" should be --using--

Signed and Sealed this

First Day of November 1983

[SEAL]

Attest:

GERALD J. MOSSINGHOFF

Attesting Officer     Commissioner of Patents and Trademarks